US00PP30594P3

(12) United States Plant Patent
Wood

(10) Patent No.: US PP30,594 P3
(45) Date of Patent: Jun. 25, 2019

(54) ***BERBERIS* PLANT NAMED 'SMBTM'**

(50) Latin Name: *Berberis thunbergii*
Varietal Denomination: SMBTM

(71) Applicant: Timothy Wood, Spring Lake, MI (US)

(72) Inventor: Timothy Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 15/732,262

(22) Filed: Oct. 16, 2017

(65) Prior Publication Data

US 2019/0116702 P1 Apr. 18, 2019

(51) Int. Cl.
*A01H 5/12* (2018.01)

(52) U.S. Cl.
USPC ..... Plt./241

(58) Field of Classification Search
USPC ..... Plt./241
CPC ... A01H 5/12; A01H 5/00; A01H 5/02; A01H 5/08; A01H 6/00
See application file for complete search history.

(56) References Cited

PUBLICATIONS

Monrovia Lava Nugget Barberry 2018, retrieved on Sep. 8, 2018, retrieved from the Internet at https://www.monrovia.com/plant-catalog/plants/5552/lava-nugget-barberry/, 2 pp. (Year: 2018).*

* cited by examiner

*Primary Examiner* — June Hwu
(74) *Attorney, Agent, or Firm* — Cassandra Bright

(57) ABSTRACT

A new and distinct *Berberis* cultivar named 'SMBTM' is disclosed, characterized by red new growth that turns to burgundy, compact rounded habit and red/orange fall color. The new variety is a *Berberis*, normally produced as an outdoor garden or container plant.

2 Drawing Sheets

Latin name of the genus and species: *Berberis thunbergii*.
Variety denomination: 'SMBTM'.

BACKGROUND OF THE INVENTION

The new *Berberis* cultivar is a product of a planned breeding program conducted by the inventor, Timothy D. Wood, in Grand Haven, Mich. The objective of the breeding program was to produce new *Berberis* varieties. The cross resulting in this new variety was made during June of 2003.

The seed parent is an unpatented, commercial variety *Berberis thunbergii* 'Concorde'. The pollen parent is unknown, as it was an open pollination breeding program. The new variety was identified as a potentially interesting selection in June of 2006, at a commercial greenhouse in Grand Haven, Mich.

Asexual reproduction of the new cultivar 'SMBTM' by softwood to semi-hardwood cuttings was first performed during the June of 2006, at a commercial greenhouse in Grand Haven, Mich. Subsequent propagation has shown that the unique features of this cultivar are stable and reproduced true to type in 4 successive generations.

SUMMARY OF THE INVENTION

The cultivar 'SMBTM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMBTM'

These characteristics in combination distinguish 'SMBTM' as a new and distinct *Berberis* cultivar:

1. Red new growth that turns to burgundy.
2. Compact, rounded habit.
3. Red/orange fall colors.

PARENT COMPARISON

Plants of the new cultivar 'SMBTM' are similar to plants of the seed parent, unpatented, commercial variety *Berberis thunbergii*, 'Concorde' in most horticultural characteristics, however, plants of the new cultivar 'SMBTM' differ in the following;

1. Burgundy red foliage. The seed parent has dark plum foliage.
2. Compact spreading/rounded habit. The seed parent has a tight compact habit.

Pollen parent unknown as this is product of open pollination.

COMMERCIAL COMPARISON

Plants of the new cultivar 'SMBTM' can be compared to the unpatented commercial variety *Berberis* 'Crimson Pygmy'. These varieties are similar in most horticultural characteristics; however 'SMBTM' differs in the following:

1. The new variety has a more spreading habit.
2. The new variety has a burgundy/red leaf color, whereas the comparator has a burgundy leaf color.

BRIEF DESCRIPTION OF THE PHOTOGRAPHS

Figure 1:
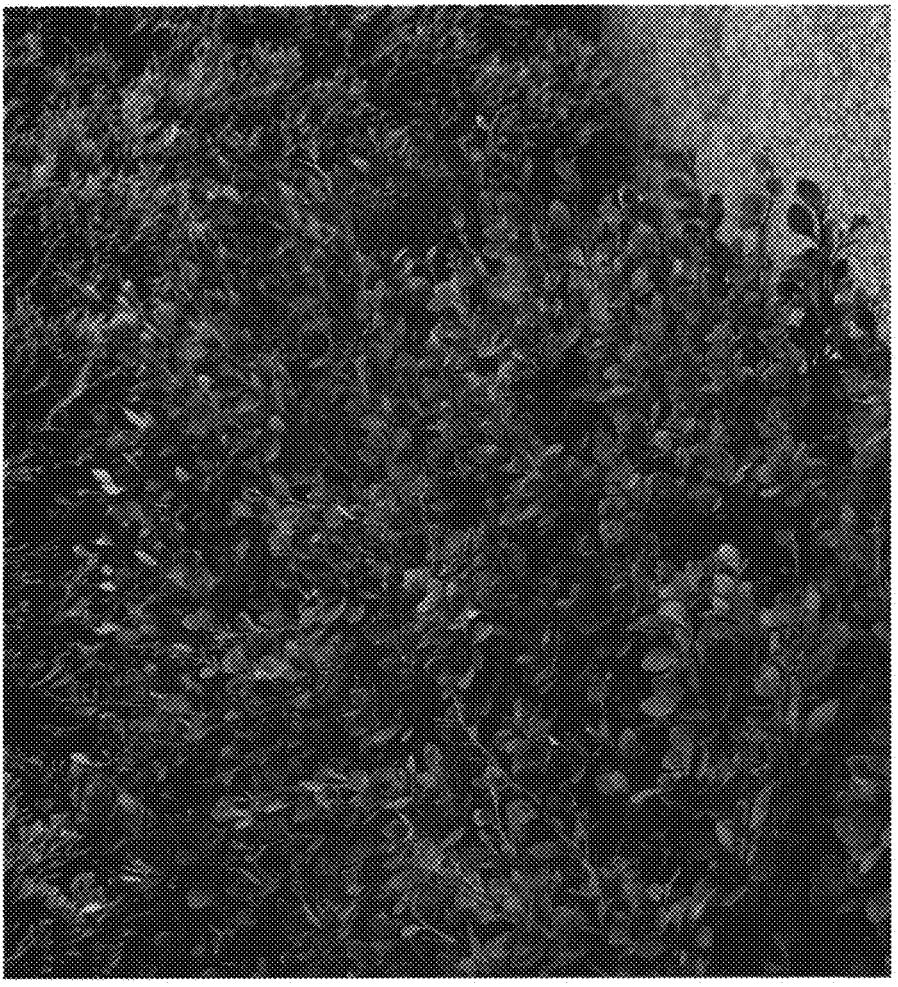

The accompanying photograph in FIG. 1 illustrates in full color a typical plant of 'SMBTM' grown in an outdoor flower bed, in Dayton, Oreg., foliage shown is both new, with red coloration and more mature, colored burgundy.

Figure 2:
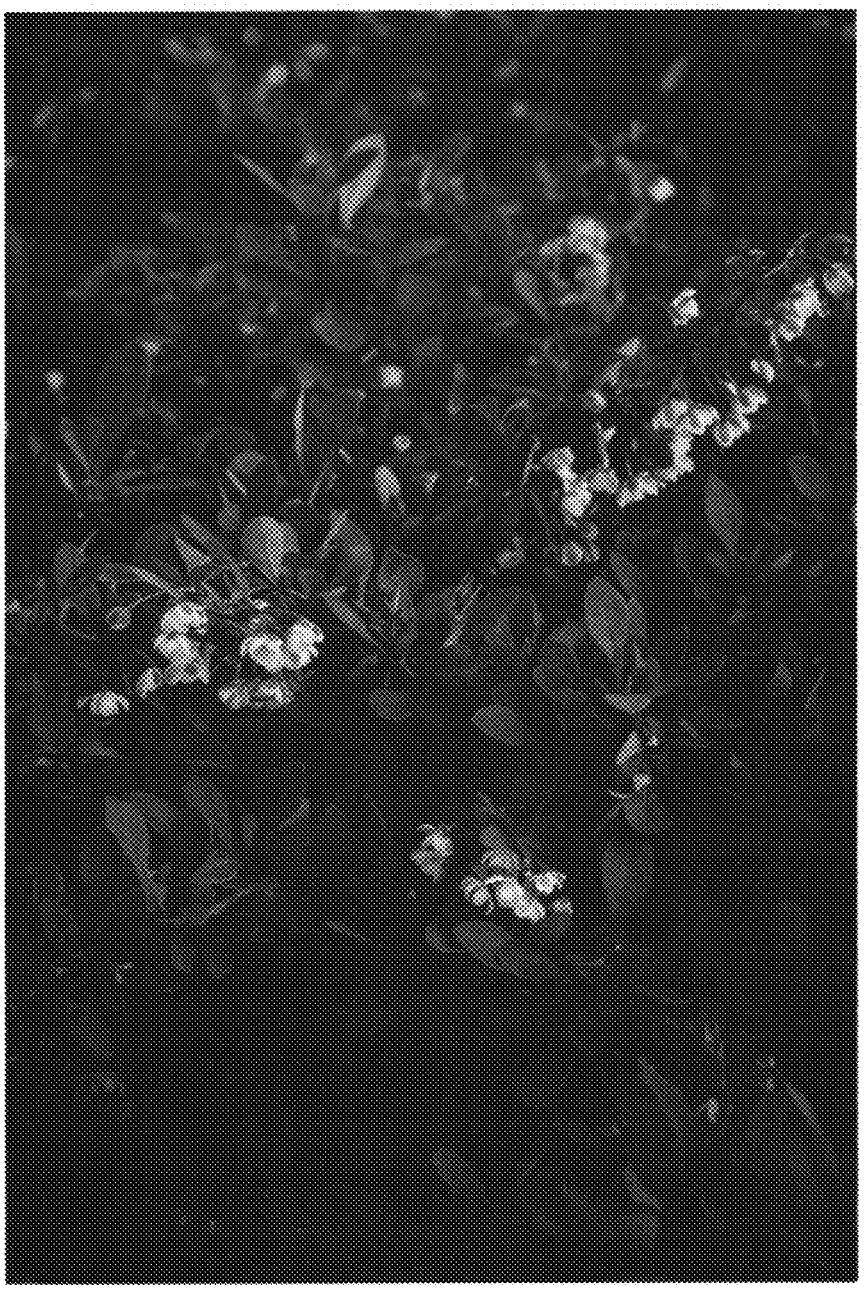

FIG. 2 illustrates in full color a close up view of typical foliage and foliage of 'SMBTM'. Age of the plant photographed is approximately 2 to 3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SMBTM' plants grown out doors and also in a commercial poly greenhouse in Grand Haven, Mich. under natural lighting. Measurements were taken during the Spring and Summer of 2015. The plants were 2-3 years old in 1 gallon containers and field grown. The growing temperature ranged from 5° C. to 27° C. Measurements and numerical values represent averages of typical plant types.

Botanical classification: *Berberis thunbergii* 'SMBTM'.

Propagation:

*Time to initiate roots.*—About 20 days at approximately 27° C.

*Root description.*—Density is moderate to dense, fibrous, freely branching. Medium root thickness. White to brown in color, not effectively measured with a color chart.

*Time to produce a rooted young plant.*—About 90 days at 27° C.

Plant:

*Plant type.*—Perennial deciduous shrub.

*Age of plant described.*—Approximately 2-3 years old.

*Growth habit.*—Good.

*Pot size of plant described.*—1 gallon nursery pot, also field grown plants.

*Overall plant shape.*—Upright/rounded.

*Height.*—55 cm in 4 year old field plant.

*Plant spread.*—100 cm in 4 year old field plant.

*Growth rate.*—Good.

*Plant vigor.*—Good.

*Branching characteristics.*—Upright, strong basal branching. Pinching required.

*Length of primary lateral branches.*—45-55 cm in 4 year old field plant.

*Diameter of lateral branches.*—3 mm.

*Quantity of lateral branches.*—30-40, 4 year old field plant.

*Stem.*—Stem Appearance: Oval. Stem Strength: Strong. Bark: Near RHS Brown 200A. Pubescence: None. Aspect: 0-45°.

*Internode length.*—0.5-1 cm.

Foliage:

*Leaf.*—Arrangement: Whorled, single. Leaf shape: Ovate. Average Length: 2-2.5 cm. Average Width: 1-1.25 cm. Apex: Acute to obtuse. Base: Attenuate. Margin: Entire. Texture of top surface: Smooth, glabrous, coriaceous. Texture of bottom surface: Smooth, glabrous. Color: Young foliage upper side: Near RHS Greyed-Red 181A, with an overlay of Red 46D. Young foliage under side: Near RHS Greyed-Red 179B, veins near Greyed-Purple 183A. Mature foliage upper side: Near RHS Greyed-Purple 183C, with an overlay Greyed-Purple 187A. Mature foliage under side: Near RHS Green 138B with soft shading of Greyed-purple 187A. Interior foliage, with low light exposure: Mature foliage upper side: Near RHS Yellow-Green 147B, upper section flushed Greyed-Purple 187A. Mature foliage under side: Near RHS Green 138A. Fall Color: Varies by environmental conditions. The following colors are representative of foliage on plants grown in Grand Haven Mich., foliage measured during the first week of October. Fall foliage upper side: Near RHS Greyed-Red 179A, base Greyed-Orange N170B. Overall slightly flushed Greyed-Orange N172D. Fall foliage under side: Near RHS Greyed-Orange N167C flushed Greyed-Red 179A.

*Venation.*—Pattern: Pinnate. Color upper side: Same as leaf color. Color under side: Same as leaf color.

*Petiole.*—Average Length: 0.75-1 cm. Diameter: 1 mm. Petiole color upper side: Near RHS Green 138B with Greyed-purple 187A base. Petiole color lower side: Near RHS Green 138B. Petiole Texture upper side: Smooth. Petiole Texture lower side: Smooth.

*Thorns.*—Form: Attached to plant nodes 1 cm in length. Simple. Color new: Near RHS Red-purple 60A. Color mature: Near RHS Grey 201A.

Flower:

*Natural flowering season.*—Spring.

*Inflorescence type and habit.*—Umbellate Fascicles.

*Flower longevity on plant.*—2 weeks.

*Quantity of flowers per inflorescence.*—1-3.

*Quantity of flowers per plant.*—108.

*Individual flowers.*—Flower shape: Star shaped. Flower aspect: Outwardly to drooping. Flowering arrangement: Terminal. Size: Diameter: Approximately 5 mm. Depth: Approximately 9 mm. Flower Other Characteristics: Persistence: Self cleaning. Fragrance: Not noted.

*Bud.*—Shape: Rounded, globose. Length: 3-4 mm. Diameter: 3-4 mm. Color: Near RHS Greyed-purple 187A.

*Petal.*—Petal arrangement: Whorl. Number of petals per flower: 5-6. Petal Shape: Elliptic. Petal Base: Obtuse. Margin: Entire. Tip shape: Obtuse. Length: 4 mm. Width: 3 mm. Texture: Upper: Smooth. Lower: Smooth.

*Petal color.*—When opening: Upper surface: Near RHS Yellow 12C. Lower surface: Near RHS Yellow 12C. Fully opened: Upper surface: Near RHS Yellow 12C. Lower surface: Near RHS Yellow 12D.

*Sepal.*—Arrangement: Whorl. Appearance: Smooth. Number: 6. Shape: Roughly orbicular. Tip: Acute to obtuse. Base: Acute to obtuse. Margin: Entire. Length: 4 mm. Width: 3 mm. Texture, Upper: Smooth. Texture, Lower: Smooth. Color: When opening: Upper surface: Near RHS Yellow 8B with center blotch close to Red 46A to 46B. Lower surface: Near RHS Yellow 8C, faint center blotch near Red 46D. Fully opened: Upper surface: Near RHS White 155A with center blotch close to Red 53B. Lower surface: Near RHS Yellow 28D with faint center blotch near Red 53C.

*Peduncle*.—Length: 6 mm. Diameter: About 0.8 mm. Color: Near RHS Yellow-Green 146B. Orientation: Upright/outward. Strength: Good. Texture: Smooth/glabrous.

Reproductive organs:

*Stamens*.—Number: 6. Filament length: about 1 mm. Filament color: Near RHS green 137B.

*Anthers*.—Shape: Globular. Length: About 1 mm. Color: Near RHS Yellow 12A. Pollen color: Near RHS Yellow 12A. Pollen amount: Some.

*Pistil*.—Number: 1 per flower. Length: about 3 mm. Style: Length: About 3 mm. Color: Near RHS Green-white 157B. Stigma: Color: Near RHS Green-white 157B.

Other characteristics:

*Seeds and fruits*.—1-3 fruit per branch. 20 fruit per plant. Average fruit length 1 cm, average fruit diameter 6 mm berries colored near Orange-Red N34A. Seed production not observed to date.

*Disease/pest resistance*.—Neither resistance nor susceptibility to normal diseases and pests of *Berberis* have been observed.

*Temperature tolerance*.—The new variety tolerates temperatures between −31° C. to 38° C.

What is claimed is:

1. A new and distinct cultivar of *Berberis* plant named 'SMBTM' as herein illustrated and described.

* * * * *